United States Patent [19]
Sassi

[11] Patent Number: 5,578,580
[45] Date of Patent: Nov. 26, 1996

[54] VETERINARY COMPOSITION, FEEDSTUFF AND PROCESS

[75] Inventor: Graziano Sassi, Bertinoro, Italy

[73] Assignee: Ascor Chimici S.r.l., Forli, Italy

[21] Appl. No.: 560,945

[22] Filed: Nov. 20, 1995

Related U.S. Application Data

[63] Continuation of Ser. No. 250,505, May 27, 1994, abandoned.

[30] Foreign Application Priority Data

May 28, 1993 [EP] European Pat. Off. ............. 93830239

[51] Int. Cl.$^6$ .................................................. A61K 31/70
[52] U.S. Cl. ............... 514/29; 514/951; 514/963
[58] Field of Search ................. 514/29, 951, 963

[56] References Cited

U.S. PATENT DOCUMENTS

| | | | |
|---|---|---|---|
| 2,653,899 | 4/1952 | Bunch et al. | 536/7.2 |
| 2,823,203 | 2/1958 | Clark, Jr. | 536/7.5 |
| 3,876,551 | 4/1975 | Laufer et al. | 252/98 |
| 4,102,806 | 7/1978 | Kondo et al. | 428/402.2 |
| 4,123,382 | 10/1978 | Morse et al. | 427/213.32 |
| 4,390,448 | 6/1983 | Boden et al. | 252/187.26 |

FOREIGN PATENT DOCUMENTS

| | | |
|---|---|---|
| 349514 | 1/1990 | European Pat. Off. . |
| 419121 | 3/1991 | European Pat. Off. . |

OTHER PUBLICATIONS

CVP "Compendium of Veterinary Products," Third Edition 1995–1996, publisher Adrian J. Bayley, published by North American Compendiums Inc., pp. 10–13, 467–469, 548–550 and 1133.

Deasy, P. B., *Microencapsulation and related drug processes,* 1984, pp. 186–188.

Database WPI, Week 7450, JP 49 042 477—Nov. 15, 1974—abstract.

Database WPI, Week 9025, RO 98 055—Oct. 30, 1989—abstract.

WO–A–9 221 249—p. 7, Line 3—Line 6; claims 1,6–13 (Feb., 18, 1993).

*Primary Examiner*—Kevin E. Weddington
*Attorney, Agent, or Firm*—Cushman Darby & Cushman, L.L.P.

[57] ABSTRACT

A veterinary composition in form of sustained release microcapsules containing erythromycin thiocyanate as active ingredient is disclosed. In the use, said composition is mixed with standard feedstuff in a ratio of 100/200 g per 100 kg (quintal) feedstuff. A process for preparing said composition is also disclosed.

16 Claims, No Drawings

VETERINARY COMPOSITION, FEEDSTUFF AND PROCESS

This application is a continuation of Ser. No. 08/250,505 filed May 27, 1994; now abandoned.

BACKGROUND OF THE INVENTION

The present invention relates to a veterinary composition in microencapsulated form useful for preventing and/or treating diarrhea or abortion, infections caused by gram-positive cocci and rods, anaerobic infections, rickettsial and chlamydial infections, and mycoplasma infections, More particularly it relates to a composition in the form of sustained release microcapsules to treat and prevent swine dysentery and containing erythromycin thiocyanate as active ingredient as well as a feedstuff containing said composition and a process for preparing the same.

It is known that by swine dysentery a common, important mucohemorrhagic diarrheal and exudative disease is meant, which occurs in most swine-producing countries. A spirochete, *Treponema hvodvsenteriae*, is the only agent involved in the transmission of swine dysentery, but other anaerobic bacteria that are normally present in the colon of pigs are necessary in addition to *T. hyodvsenteriae* to produce the disease in gnotobiotic pigs.

The disease is transmitted by ingestion of fecal material from affected or clinically normal swine caring *T. hyodysenteriae*. New outbreaks in herds from which the disease was previously absent usually follow the introduction of new stock. Once the disease has entered a herd, it usually spreads slowly at first, requiring close contact between pigs or the movement of relatively large amounts of infective feces. It may take several weeks or months to build up to a high morbidity. It remains permanently endemic and is difficult to eradicate. Any age of pig is susceptible but the incidence is highest between 15 and 17 kg. The incubation period is usually 7 to 14 days, but it may be considerably longer. In field cases the death rate in weanling pigs may be as high as 30% and the morbidity over 90% but in most cases the mortality is low and the morbidity about 25 to 50%.

The first evidence of the disease in most herds is the appearance of yellow-to-gray, soft feces combined with a slight reduction in appetite. As the disease progresses the feces may become watery, contain blood, mucus and a whitish mucofibrinous exudate, with staining of the perineal region; this leads to dehydration, weakness, emaciation, rough coat, incoordination and increased thirst. The body temperature may rise, however this is not consistent. The diffuse lesions are confined to the cecum, spiral colon, and rectum. In early stages, the affected mucosa is covered with a layer of transparent or gray mucus, often with suspended flecks of blood. More advanced cases have a a mixture of blood, fibrin, and necrotic debris adhered to the mucosal surface. Late in the course, yellow, necrotic debris is on the mucosal surface.

Where repopulation is impractical, the disease must be controlled by strict attention to hygiene, husbandry, prevention of stress and overcrowding and the judicious use of drugs. Several chemotherapeutic agents are useful as feed additives for the prophylaxis of swine dysentery; they include carbadox, lincomycin, arsanilic acid, virginiamycin, tylos in, and others. All these compounds must be used in conjunction with good husbandry and hygienic practices. They are most effective in keeping the disease subclinical, after the overt clinical signs have been controlled by water medication.

In recent years, however, for the treatment and prevention of many infections, and above all for swine dysentery, erythromycin thiocyanate has been strongly proposed. In comparison with tylosine and for example erytromycin estolate, erhythromycin thiocyanate has in fact the advantage to be an inexpensive material, so that its use would be of high interest thereby reducing the treatment costs.

Erythromycin is an antibiotic substance produced by a strain of *Streptomyces ervthreus* found in a soil sample from the Philippine Archipelago (U.S. Pat. No. 2,653,899 and 2,823,203 to Lilly and Abbott respectively). There are three erythromycins produced during fermentation, designated A, B and C; A is the major and most important component. Erythromyc in A and B contain the same sugar moieties, desosamine and cladinose. They differ in position 12 of the aglycone, erythronolide, A having an hydroxyl substituent. Component C contains desosamine and the same aglycone present in A but differs by the presence of mycatose instead of cladinose. In the above and following description, with erythromycin always erythromycin A is meant unless other specified.

However, the use of erythromycin thiocyanate as chemotherapeutic agent has not met with the consumers' approval. In fact, owing to its very unpleasant taste and smell, it is absolutely refused by all the animals having a developed olfactory and taste sense, such as for example pigs and fishes, dogs, cats, horses, etc.

Numerous attempts have been made to remove or mask erythromycin thiocyanate's unpleasant taste and to formulate a composition well accepted for example by pigs, but all efforts have proved unsuccessful. Surprisingly, It has now been found that by treating erythromycin thiocyanate with selected additives, a composition can be obtained that is suitable for preparing a feedstuff able to treat and/or prevent many infections in animals, particularly the swine dysentery.

BRIEF SUMMARY OF THE INVENTION

The object of the present invention is accordingly to provide a composition in microencapsulated form for the treatment and/or prevention of diarrhea or abortion, infections caused by gram-positive cocci and rods, anaerobic infections, rickettsial and chlamydial infections, mycoplasma infections, and particularly of swine dysentery, said composition comprising a) erythromycin thiocyanate, b) a vegetal or animal proteic meal, c) a natural or synthetic sweetening agent, d) a film former selected from the group consisting of fatty acids with 12–22 carbon atoms, mono or diglycerides, waxes, solid hydrogenated and non-hydrogenated oils and fats, solid high alcohols, solids polyethylenglicols, and eventually e) an aromatizer.

DESCRIPTION OF THE PREFERRED EMBODIMENTS

In all the preparations, erythromycin thiocyanate having an activity of 800 mg/g has been employed, so that an end-product having an erythromycin activity of 100 mg/g has been obtained. Erythromycin is present in the composition in an amount of from 50 to 500 g, based on 1000 g of composition.

As vegetal or animal proteic meal, fish meal could be employed in an amount of from 10 to 200 g based on 1000 g of composition.

As sweetening agents any of the well known natural or synthetic sweeteners could be employed, such as fructose, glucose, sucrose, aspartame, saccharin, saccharin sodium. Its level in the composition is of from 1 to 100 g based on 1000 g of composition. Micronized saccharin sodium is preferred.

As aromatizer any of the well known types currently allowed by law can be used. Suitable aromatizers are available from such manufacturers as Quest, International Flavors and Fragrances, Givaudan and Firmenich, Inc. Examples thereof which may be suitable for use are described in U.S. Pat. No. 3,876,551 and U.S. Pat. No. 4,390,448. If utilized, these aromatizers will generally comprise from 1 to 100 g based on 1000 g of composition.

As film lochner under e) any compound selected from the group consisting of fatty acids with 12–22 carbon atoms, mono and diglicerides, waxes, solid hydrogenated and non-hydrogenated oils and fats, solid high alcohols and polyethilenglicoles in an amount of from 450 to 900 g could be employed, said amount being based on 1000 g of composition. As waxes, white wax USP, canauba wax, synthetic wax-like ester (marketed as Glycowax S-392 from Glyco Chemical Inc., New York, N.Y.), glyceryl tristearate, hydrogenated castor oil, cetyl alcohol NF and glyceryl monostearate are preferred. The oil and fat is mainly composed of glycerin ester of fatty acids ( Encyclopedia of Polymer Science and Technology, John Wiley & Sons Inc. Vol, 1,98). The oil and fat usable in this invention is solid at room temperature and has a melting point not lower than 30° C., preferably not lower than 50° C., and further preferably not lower than 60° C. It may be exemplified by hydrogenareal castor oil, hydrogenareal soybean oil, hydrogenareal rapeseed oil, hydrogenated beef tallow, hydrogenated cottonseed oil, hydrogenated fishoil, hydrogenated whale oil, cacao butter, lard, beef tallow, palm oil, sesame oil, safflower oil peanut oil and coconut oil.

As fatty acids, palmitic acid, stearic acid, lauric acid and myristic acid are preferred. In a preferred embodiment, the invention titus provides a veterinary composition in microencapsulated form, particularly for the treatment and prevention of the swine dysentery, comprising a) from 50 to 500 g of erythromycin thiocyanate,
b) from 10 to 200 g of vegetal or animal proteic meal,
c) from 1 to 100 g of sweetening agent,
d) from 450 to 900 g of film former, and eventually
e) from 1 to 100 g of an aromatizer, all the weights being based on 1000 g of the finished composition.

In another preferred embodiment the invention provides a veterinary composition in microencapsulated form, particularly for the treatment and prevention of the swine dysentery, comprising a) from 50 to 500 g of erhyt/mromycin thiocyanate,
b) from 10 to 200 g of fish meal,
c) from 1 to 100 g of sacc. harin sodiums,
d) from 450 to 900 g of a film former selected from the group consisting of fatty acids with 12–22 carbon atoms, mono and diglicerides, solid polyethylenglicols, waxes, solid hydrogenated and non-hydrogenated oils and fats, solid high alcohols, and eventually
e) from 1 to 100 g of an aromatizer, all the weights being based on 1000 g of the finished composition.

The invention further provides a process for preparing the above mentioned composition in microencapsulated form, said process comprising the steps of charging first the film former substance e) in a reaction vessel, and when said film former has melted, adding the other ingredients, stirrirg all the time. At the end of the reaction, the product thus obtained is transferred in an atomizer to produce microspheres having a size of 20–1,200 microns.

Even though the microencapsulation technique is well known in the art (U.S. Pat. No. 4,123,382; U.S. Pat. No. 4,102,806; Microencapsulation and related drug processes, by P. B. Deasy, Marcel Dekker Inc., New York, N.Y. ) and the conventional spray dryers operating with a cool inlet air are used for this purpose, a granule for the control led and sustained release of erythromycin thiocyanate had not been yet described. Anyway, also in the present case feed rates and temperatures conditions are adjusted to insure rapid congealing of the atomized droplets. The powder collected as product consists of individual, more or less spherical particles, each of which contains bits of active ingredient suspended in a matrix of the coating agent.

The composition in the form of microcapsules is then mixed with a standard feedstuff in a ratio of composition to feedstuff preferably of 100/200 g microcapsules per 100 kg feedstuff.

The following detailed examples describe how to prepare the composition of the present invention and is to be construed as merely illustrative and not limitative of the preceding disclosure. A person skilled in the art will promptly recognize appropriate variations from the above description both as to reactants and as to reaction conditions and techniques.

EXAMPLE 1

In a reactor fitted with thermometer, blade stirrer, addition vessel and equipped with heating means consisting mainly of oil heated coils or jackets 778 kg palm oil (melting point: 56°–60° C.) were charged. The inner temperature was elevated at 130° C. and the content was stirred for about 5 hours until a homogenous melt was obtained. The temperature was then decreased at 72° C. and through addition vessels 70 kg fish meal, 10 kg saccharin sodium and 132 kg erythromycin thiocyanate were added, stirring all the time. The react ion was continued for one hour, and the product thus obtained was transferred by means of heated pumps and insulated lines to nozzles for atomizing the liquid mixture in a cool chamber.

The apparatus operates with cool, dry inlet air and the feed rates were varied from 35 to 320 g per minute. The end product was collected in a cyclone at the bottom of the chamber and sieved. The particle size was found to correspond to the size of nozzles used, while wax-like ester formulations produced the smallest particles. In this way it is possible to have more or less spherical particles having a mean diameter of from 20 to 1200 microns. They are light brown-yellow colored with a slight fishy odor.

The product was mixed with a standard pig feedstuff in the ratio of 100/200 g of microcapsules per 100 kg feedstuff. The mixture was given to just weaned pigs suffering from bacterial infections of the intestine. The treatment lasted 21 days, and at the end of the administration the infection disappeared.

EXAMPLE 2

In this example, the Basic Formulation of Example 1 was modified by adding aspartame instead of saccharin sodium and 10 kg of aromatizer, The product thus obtained was given to goldfish suffering from a not well-diagnosed form of diarrhea. After 9 days' treatment the infection disappeared.

EXAMPLE 3

In this example, the Basic Formulation of Example 1 was modified by adding stearic acid and sucrose instead of saccharin sodium and palm oil respectively. Microcapsules having a size of 700 microns were obtained, which proved to be very active in treating enteritis in dogs and cats.

What is claimed:

1. A veterinary composition comprising
   a) from 50 to 500 g of erythromycin thiocyanate,
   b) from 10 to 200 g of animal or vegetal proteic meal,
   c) from 1 to 100 g of a sweetening agent, and
   d) from 450 to 900 g of a film former, which composition is in the form of sustained release microcapsules between 20 and 1200 microns in size, and which composition when administered to an animal masks the taste and smell of the erythromycin thiocyanate and is thereby palatable to the animal.

2. A composition as in claim 1, wherein the proteic meal is fish meal.

3. A composition as in claim 1, where in the sweetening agent is selected from the group consisting of aspartame, saccharin, saccharin sodium, fructose, sucrose and lactose.

4. A composition as in claim 3, wherein the sweetening arent is saccharin sodium.

5. A composition as in claim 1, wherein the film former is selected from the group consisting of fatty acids with 12–22 carbon atoms, mono and diglycerides, waxes, solid hydrogenated and non-hydrogenated oils and fats, solid high alcohols, solid polyethylenglicols.

6. A composition as in claim 5, wherein the film former is stearic acid.

7. A composition as in claim 5, wherein the film former is palm oil, hydrogenated castor oil, hydrogenated soybean oil, hydrogenated rapeseed oil, hydrogenated cottonseed oil or hydrogenateal fish oil.

8. A composition as in claim 1, which further comprises from 1 to 100 g of an aromatizer.

9. A veterinary composition comprising
   a) from 125 to 140 grams of erythromycin thiocyanate,
   b) from 60 to 80 grams of fish meal,
   c) from 5 to 20 grams of saccharin sodium,
   d) from 600 to 800 grams of palm oil, and
   e) from 5 to 20 grams of an aromatizer, all the weights being based on 1000 grams of composition, which composition is in the form of sustained release microcapsules between 20 and 1200 microns in size, and which composition when administered to an animal masks the taste and smell of the erythromycin thiocyanate and is thereby palatable to the animal.

10. A veterinary composition comprising
    a) 132 grams of erythromycin thiocyanate,
    b) 70 grams of fish meal,
    c) 10 grams of saccharin sodium,
    d) 778 grams of palm oil, and
    e) 10 grams of an aromatizer, all the weights being based on 1000 grams of composition, which composition is in the form of sustained release microcapsules between 20 and 1200 microns in size, and which composition when administered to an animal masks the taste and smell of the erythromycin thiocyanate and is thereby palatable to the animal.

11. Animal feedstuff comprising:
    a given feedstuff, containing from 100 to 200 grams of a composition in the form of sustained released microcapsules with a size of 20 to 1200 microns and comprising:
    a) from 50 to 500 grams of erythromycin thiocyanate,
    b) from 10 to 200 grams of animal or vegetal proteic meal,
    c) from 1 to 100 grams of sweetening agent,
    d) from 450 to 900 grams of a film former, and optionally
    e) from 1 to 100 grams of an aromatizer, all based on 1000 grams of composition, per 100 kilograms of said given feedstuff, which composition masks the taste and smell of the erythromycin thiocyanate and is thereby palatable to an animal.

12. A process for preparing a veterinary composition suitable for oral administratin to an animal, which comprises the steps of:
    a) melting 45–90 parts by weight film former in a reaction vessel,
    b) adding 5–50 parts of weight erythromycin thiocyanate, 0.1–10 parts by weight sweetening agent, 1–20 parts by weight proteic meal and 0.1–10 parts by weight aromatizer while stirring, and
    c) transferring the mixture obtained in step b) into an atomizer to form sustained release microcapsules having a size of from 20 to 1200 microns, and thereby obtain the veternary composition suitable for oral administration to an animal.

13. A process as in claim 12, wherein the film former is selected from the group consisting of fatty acids with 12–22 carbon atoms, mono and diglicerides, waxes, solid hydrogenated and non-hydrogenated oils and fats, solid higher alcohols, and solid polyethylenglicols.

14. A process as in laim 13, wherein the film former is palm oil.

15. A process as in claim 12, wherein the proteic meal is fish meal.

16. A process as in claim 12, wherein the sweetening agent is saccharin sodium.

* * * * *